(12) United States Patent
Chang et al.

(10) Patent No.: US 6,271,412 B1
(45) Date of Patent: Aug. 7, 2001

(54) PHOTOSENSITIVE MONOMER

(75) Inventors: Shang-Wern Chang, Taipei; Yen-Cheng Li, Sanchung; Shang-Ho Lin, Taipei, all of (TW)

(73) Assignee: Everlight USA, Inc., Pineville, NC (US)

( * ) Notice: Subject to any disclaimer, the term of this patent is extended or adjusted under 35 U.S.C. 154(b) by 0 days.

(21) Appl. No.: 09/608,603

(22) Filed: Jun. 30, 2000

(51) Int. Cl.⁷ .................................................. C07C 69/52
(52) U.S. Cl. ......................... 560/220; 560/129; 560/205; 526/282; 522/42; 428/64; 428/412
(58) Field of Search .................................. 560/220, 129, 560/205; 526/282; 522/42; 428/64, 412

(56) References Cited

U.S. PATENT DOCUMENTS

| 4,591,626 | * | 5/1986 | Kawai et al. | 526/282 |
| 4,937,118 | * | 6/1990 | Inagaki et al. | 428/64 |
| 5,318,850 | * | 6/1994 | Pickett et al. | 428/412 |

OTHER PUBLICATIONS

Landa et al., "Adamantane and derivatives. IX. The 2–substituted derivatives," in Collect. Czech. Chem. Commun. (1967), 32(2), 570–5. (CA 1967:55094).*

* cited by examiner

*Primary Examiner*—Ralph Gitomer
*Assistant Examiner*—D. Khare
(74) *Attorney, Agent, or Firm*—Bacon & Thomas, PLLC

(57) ABSTRACT

This invention provides a compound of the formula (I):

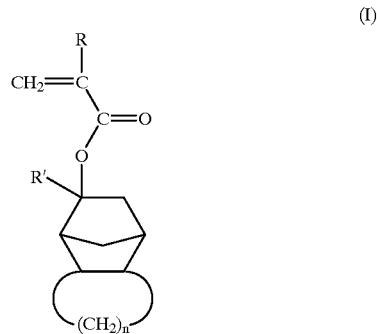

wherein R is hydrogen or $C_1$–$C_4$ alkyl group; R' is $C_1$–$C_4$ alkyl group; n is an integer of 2, 3, 4, 5 or 6. The compound of formula (I) can be polymerized or copolymerized to form a photosensitive polymer or copolymer.

9 Claims, No Drawings

PHOTOSENSITIVE MONOMER

FIELD OF THE INVENTION

The present invention relates to a novel compound. Especially relates to a photosensitive monomer.

BACKGROUND OF THE INVENTION

Current semiconductor industry trends indicate that availability of lithography below 0.18 μm is required for the development of high performance logic processors and 1-Gbit DRAM. In theory, there are two possible ways to get resist patterns with finer resolution, i.e. to shorten the wavelength of exposure light sources and to enlarge the numerical aperature (NA) of exposure systems.

KrF excimer laser (248 nm) steppers are widely used for the 0.25 μm UV lithography manufacturing process of semiconductor devices. Due to the improvement of optical elements such as high NA optical elements, phase shift mask, etc., the 248 nm KrF scanners now are capable of offering pilot run of 0.18 μm process and pioneer development of below 0.15 μm process. However, since there is a limit for wavelength shortening, the processing or manufacturing of finer masks becomes more and more difficult. To meet the urge demand of minimizing the size of IC devices, development of 193 nm (ArF excimer laser) lithography and resists are recognized as an alternative resolution recently.

Unfortunately, due to the strong absorption of aromatic rings that provides dry-etch resistance, the conventional chemical amplified resists based on phenol resin (248 nm) are totally opaque at 193 nm. To solve the problems, new polymers that exhibit low optical density at 193 nm are in great need now.

Generally speaking, the polymers which are adequate candidates for the photoresists for 193 nm lithography are required to meet six basic requirements:

(1) high transparency for 193 nm light source;
(2) good thermoplastic, ex. High glass transition temperature (Tg);
(3) high etch resistance;
(4) good adhesion and development for its composition;
(5) contained acid labile functional groups;
(6) be applied to general processes.

Recently, a tetrapolymer iBMA-MMA-tBMA-MMA (poly isobornyl methacrylate-methyl methacrylate-t-butyl methacrylate-methacrylic acid) is reported to be a possible resin system for ArF resist:

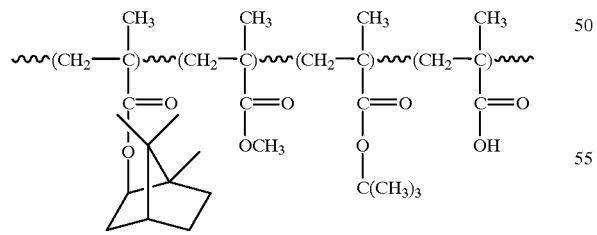

However, the tetrapolymer is also accompanied with undesirable adhesion and etch resistance. Therefore, a new resin for the compositions of resists is eager to be developed.

SUMMARY OF THE INVENTION

One object of the present invention is to provide a new monomer compound, which can be polymerized or copolymerized to be photosensitive polymers or copolymers.

The present invention provides a compound of the formula (I):

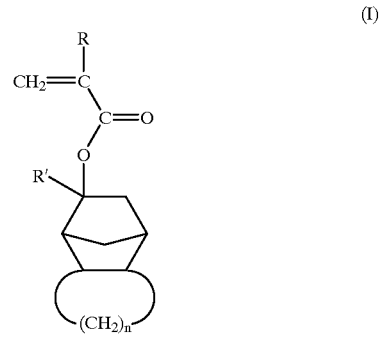

Wherein R is hydrogen or $C_1$–$C_4$ alkyl group; R' is $C_1$–$C_4$ alkyl group; n is an integer of 2, 3, 4, 5 or 6.

Compounds of formula (I) can be copolymerized together with one or more vinyl monomers to form a photosensitive copolymer. The photosensitive copolymers can be used as components of chemical amplified photoresist compositions. The polymers or copolymers polymerized or copolymerized from compound (I) can be optionally mixed with photoacid generators, acid quenchers, additives or solvents to form photoresist compositions applied for general lithography process or 193 nm lithographic process.

DETAILED DESCRIPTION OF THE INVENTION

The compound of the present invention is a compound with formula (I):

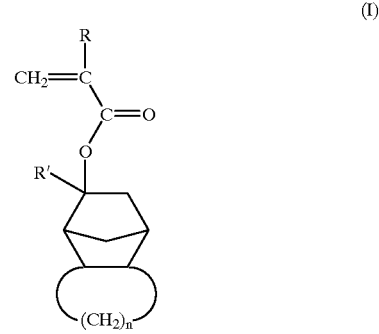

wherein R represents H or alkyl group of $C_1$–$C_4$; R' represents alkyl of $C_1$–$C_4$; n is an integer of 2, 3, 4, 5 or 6.

Preferably, compound (I) is a monomer of polycycloalkyl acrylate which can be obtained from the reaction of acryloyl chloride and tricycloalcohol or its derivatives.

Compound (I) can be polymerized to form polymers contain the following structure unit of formula (II):

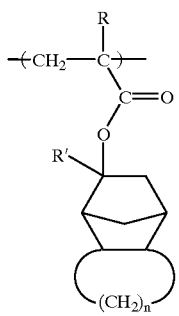

(II)

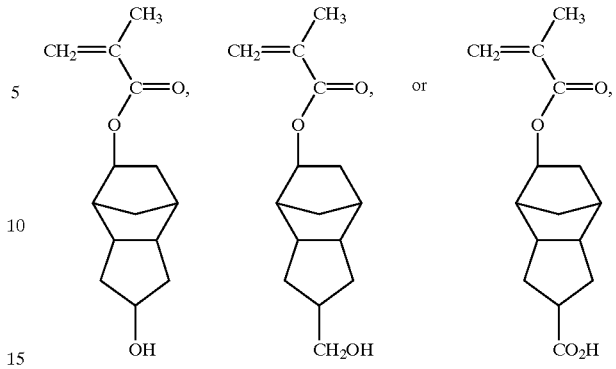

wherein R, R' and n are defined as the above.

Compound (I) also can be copolymerized with other vinyl monomers to form various copolymers with or without the assistance of catalysts.

There is no special limit for the application of the polymers or copolymers. However, if the polymers polymerized or copolymerized from compound (I) are expected to be transparent for the radiation with 193 nm wavelength, vinyl monomers free of aromatic rings are preferred.

Vinyl monomers suitable to copolymerized with compound (I) can be

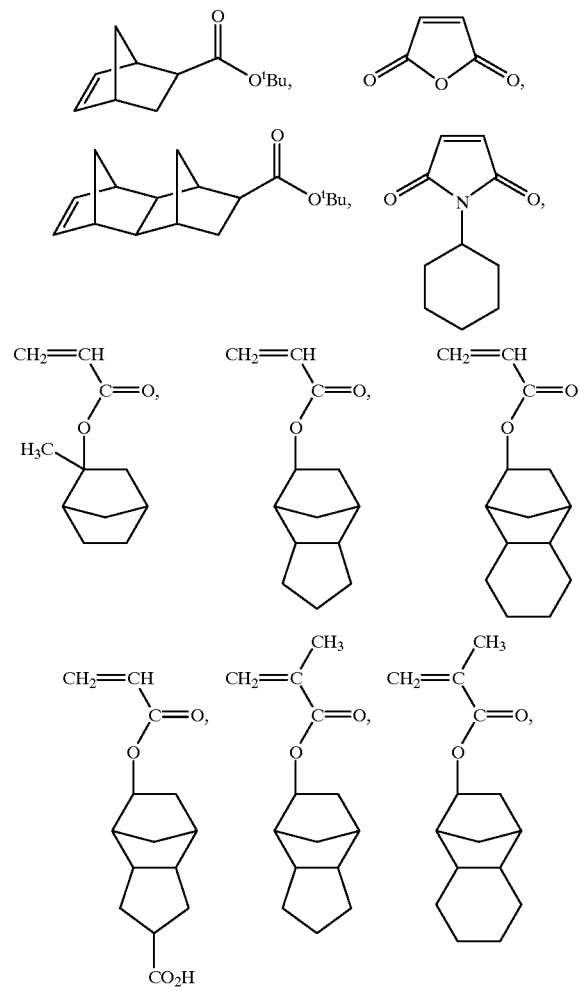

The structure unit of the polymer or copolymers polymerized or copolymerized from compound (I) can be

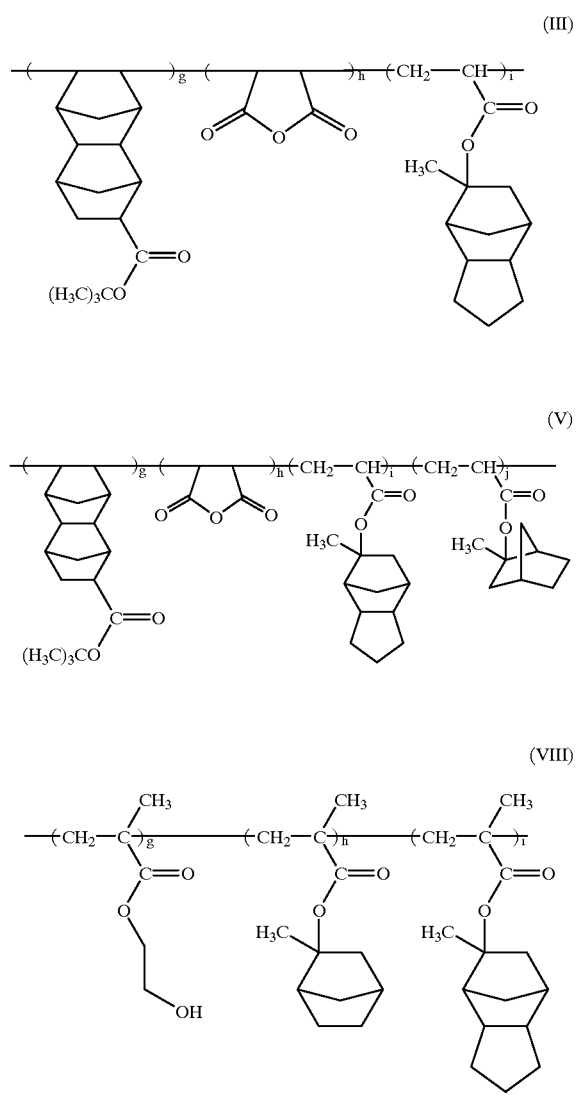

in the above structure unit of formula (III) and (VIII) wherein $g+h+i=1$, more preferably $g/(g+h+i)=0.1-0.5$, $h/(g+h+i)=0.1-0.5$, and $i/(g+h+i)=0.1-0.5$; in the above structure unit of formula (V), wherein $g+h+i+j=1$, more preferably g/(g+h+i+j)=0.1–0.5, h/(g+h+i+j)=0.1–0.5, i/(g+h+i+j)=0.1–0.5, and j/(g+h+i+j)=0.1–0.5.

There is no special limit for the synthetical method of the polymers or copolymers from compound (I) of the present invention. Preferably, the polymerization or copolymerization of compound (I) or its mixture is initiated by initiators. Initiator used here can be any initiator used by the people who is skilled in the art. Preferably, the initiator is 2,2'-azo-bis-isobutyronitrile (AIBN) or dimethyl-2,2'-azo-bis-isobutyrate radical initiator (V-601).

The polymers or copolymers of present invention can combine with adequate photoacid generator (PAG), acid quencher, additives or solvent to form chemical amplified photoresist compositions.

The chemical amplified photoresist compositions of the present invention can be used in the process of lithography. Especially, the chemical amplified photoresist compositions of the present invention can be used in the process of 193 nm (ArF excimer laser) lithography.

More detailed examples are used to illustrate the present invention, and these examples are used to explain the present invention. The examples below, which are given simply by way of illustration, must not be taken to limit the scope of the invention.

EXAMPLE 1

Synthesis of 8-methyl tricyclo [5.2.1.0$^{2,6}$] decan-8-yl methylacrylate (formula (I-1))

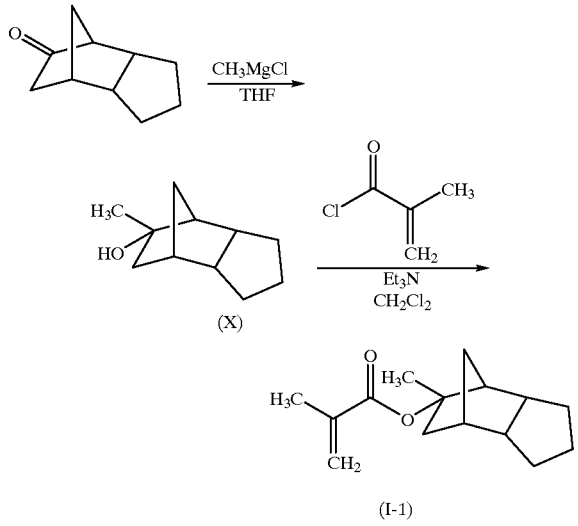

(I-1)

(1) Synthesis of 8-methyl-tricyclo [5.2.1.0$^{2,6}$] decan-8-ol (formula (X))

Tricyclo [5.2.1.0$^{2,6}$] decan-8-one (15.0 g) in tetrahydrofuran (THF, 50 ml) is slowly added into CH$_3$MgCl (9.7 g) in THF and the reaction mixture is stirred completely. Tetrahydrofuran (THF, 100 ml) with 5% of water is added into the reaction mixture. Then 100 ml of water is added to the reaction mixture. The reaction mixture is extracted by ether. The organic extract is concentrated in vacuo to yield 8-methyl-tricyclo [5.2.1.0$^{2,6}$] decan-8-ol (formula (X)) as white solid.

$^1$H-NMR (CDCl$_3$, 300 MHz); δ 2.60–2.45 (1H, m), 1.90–1.50 (8H, m), 1.28 (3H, s), 1.40–0.80 (5H, m). $^{13}$C-NMR (CDCl$_3$, 75 MHz); δ 76.9, 52.8, 46.8, 46.5, 41.8, 39.3, 32.7, 32.4, 31.8, 30.4, 27.4.

(2) Synthesis of 8-methyl tricyclo [5.2.1.0$^{2,6}$] decan-8-yl methacrylate (formula (I-1))

Methacryloyl chloride (20.9 g) and triethyl amine (20.2 g) is added to 8-methyl tricyclo [5.2.1.0$^{2,6}$] deccan-8-ol (20.0 g) in dichloromethane (200 ml) and the reaction mixture is stirred completely. Then 20 ml of water is added o the reaction mixture. Separating the CH$_2$Cl$_2$ and water layers, then the water layer was extracted with CH$_2$Cl$_2$ (200 mL×3). The organic layer was combined then wash with water till pH=7, dried over MgSO$_4$ and evaporated to dryness. The residue was purified by flash column on silica gel (n-hexane), the filtrate was evaporated to obtain 8-methyl tricyclo[5.2.1.0.$^{2,6}$] decan-8-yl methacrylate. (20 g, formula (I-1))

$^1$H-NMR (CDCl$_3$, 300 MHz); δ 5.95 (1H, brs), 5.41 (1H, brs), 2.35–2.00 (2H, m), 1.84 (3H, s), 1.84–1.51 (8H, m), 1.47 (3H, s), 1.46–0.80 (6H, m). $^{13}$C -NMR (CDCl$_3$, 75 MHz) δ 166.5, 137.4, 124.2, 86.4, 51.4, 46.6, 45.0, 40.6, 39.8, 32.4, 31.6, 31.1, 27.2, 25.5, 18.3.

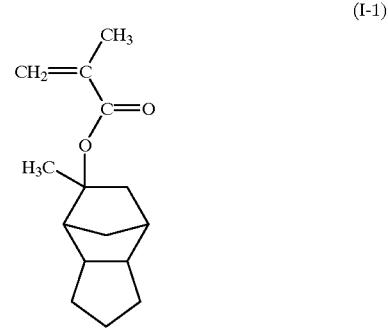

(I-1)

EXAMPLE 2

Synthesis of 8-methyl tricyclo [5.2.1.0$^{2,6}$] decan-8-yl acryloylate) (formula (I-2))

The procedure is as same as that of example 1 except methacryloyl chloride is replaced by acryloyl chloride (18.1 g). The product 8-methyl-tricyclo [5.2.1.0$^{2,6}$] decan-8-yl acrylate (18.5 g) (formula (I-2)) as colorless oil is obtained.

$^1$H-NMR (CDCl$_3$, 300 MHz); δ 6.19 (1H, dd, 17.3, 1.74), 5.90 (1H, dd, 17.3, 10.3), 5.61 (1H, dd, 10.3, 1.74), 2.29–1.44 (8H, m), 1.42 (3H, s), 1.40–0.84 (6H, m). $^{13}$C-NMR (CDCl$_3$, 75 MHz) δ 165.4, 129.8, 129.32, 86.6, 51.3, 46.6, 45.0, 40.6, 39.8, 32.4, 31.6, 31.2, 27.2, 25.5.

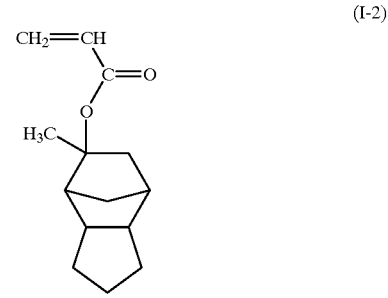

(I-2)

APPLICATION EXAMPLE 1

Synthesis of the Polymer Containing the Structure Unit of Formula (III)

(III)

wherein g+h+i=1.

The initiator (4.92 g, 2,2'-azo-bis-isobutyronitrile; AIBN) is added to the mixture of tetrahydrofuran (60 ml), tert-butyl tetracyclo [4.4.0.1$^{2,5}$. 1$^{7,12}$] dodec-3-ene-5-carboxylate (26 g), 8-methyl tricyclo [5.2.1.0$^{2,6}$] decan-8-yl acryloylate (23.4 g) and maleic anhydride (formula I-2, 9.8 g), then the mixture is heated to 70° C. and stirred overnight. Tetrahydrofuran (20 ml) is added to the mixture. After the resulted product mixture (20 ml) is added to 1 l of hexane dropwise and slowly, a white solid precipitate is obtained. The white solid is collected by filtration and dried to yield 30.23 g (51%) of the polymer containing the structure unit of formula (III), weight-average molecular weight 10875 (measured by GPC), glass transition temperature Tg=183° C., degradation temperature Td=212° C.

APPLICATION EXAMPLE 2

Synthesis of the Polymer Containing the Structure Unit of Formula (V)

(V)

wherein g+h+i+j=1.

The initiator (4.92 g, 2,2'-azo-bis-isobutyronitrile; AIBN) is added to the mixture of tetrahydrofuran (28 ml), tert-butyl tetracyclo [4.4.0.1$^{2,5}$.1$^{7,12}$] dodecan-3-ene-5-carboxylate (6.5 g), 8-methyl tricyclo [5.2.1.0$^{2,6}$] decan-8-yl acryloylate (9.7 g), 2-methyl bicyclo [2.2.1] heptan-2-yl acrylate (6.16 g) and maleic anhydride (4.9 g), then the mixture is heated to 70° C. and stirred overnight. Tetrahydrofuran (20 ml) is added to the mixture. After 20 ml of the resulted mixture is added to 1,000 ml of hexane dropwise and slowly, a white solid precipitate is obtained. The white solid is collected by filtration and dried to yield 16.58 g (54.4%) of the polymer containing the structure unit of formula (V), weight-average molecular weight 10428 (measured by GPC), glass transition temperature Tg=161° C., degradation temperature Td=208° C.

APPLICATION EXAMPLE 3

Photoresist Compositions

Triphenylsulfonium perfluoro-1-butanesul-fonate (TPS-PFBS, 0.05 g), tert -butyl cholate (TBC, 0.06 g), propylene glycol monomethyl ether acetate (10.4 g), the polymer containing the structure unit of formula (III) (2 g, obtained from Application example 1) and N-(hydroxy methyl) piperidine (0.5mg) polymer are mixed together and filtered by a 0.45 μm filter. The resulted solution is spin coated on a silicon substrate by 2200 rpm for 30 sec.

The coated substrate is dried at 130° C. for 90 seconds. The thickness of the coating is 436.8 nm. The coated substrate is exposed under 193 nm, 10~30 mj/cm$^2$ deep UV radiation and then baked on heating plate at 130° C. for 90 sec.

The exposed coating is developed by an aqueous solution of 2.38% tetramethyl ammonium hydroxide (TMAH) After the coated substrate is washed by deionized water and dried, the exposed area shows a structure of resolution of 0.15 μm under the observation of scanning electronic microscopy (SEM).

The chemical amplified photoresist compositions of the present invention can be used in lithography, especially 193 nm lithography. The resolution, shape and sensitivity of the resist pattern formed from the photoresist composition of the present invention is excellent.

From the foregoing description, one skilled in the art can easily ascertain the essential characteristics of this invention, and without departing from the scope thereof, can make various changes and modifications of the invention to adapt it to various usages and conditions. Thus, other embodiments are also within the claims.

What is claimed is:

1. A compound of the formula (I), (I)

wherein:

R is hydrogen or C$_1$–C$_4$ alkyl group; R' is C$_1$–C$_4$ alkyl group;

n is an integer of 2, 3, 4, 5 or 6.

2. The compound of claim 1, wherein said R' is methyl group.

3. The compound of claim 1, wherein said n is 3.

4. The compound of claim 1, wherein said formula (I) is 8-methyltricyclo [5.2.1.0$^{2,6}$] decan-8-yl methacrylate.

5. The compound of claim 1, wherein said formula (I) is 8-methyltricyclo [5.2.1.0$^{2,6}$] decan-8-yl acrylate.

6. The compound of claim 1, wherein R' is an ethyl group.

7. The compound of claim 1, wherein R' is a propyl group.

8. The compound of claim 1, wherein R' is a butyl group.

9. A photoresist composition containing a copolymer of a compound of claim 1 and a vinyl monomer.

* * * * *